United States Patent
Belaney et al.

(10) Patent No.: US 9,445,825 B2
(45) Date of Patent: Sep. 20, 2016

(54) EXPANDABLE SURGICAL DEVICE

(75) Inventors: Ryan M. Belaney, Oakland, TN (US);
Olaf H. Schulz, Lakeland, TN (US);
Jerry W. West, Arlington, TN (US)

(73) Assignee: WRIGHT MEDICAL TECHNOLOGY, INC., Memphis, TN (US)

(*) Notice: Subject to any disclaimer, the term of this patent is extended or adjusted under 35 U.S.C. 154(b) by 718 days.

(21) Appl. No.: 13/369,740

(22) Filed: Feb. 9, 2012

(65) Prior Publication Data
US 2012/0209274 A1 Aug. 16, 2012

Related U.S. Application Data

(60) Provisional application No. 61/441,406, filed on Feb. 10, 2011.

(51) Int. Cl.
*A61B 17/58* (2006.01)
*A61B 17/70* (2006.01)
*A61B 17/16* (2006.01)
(Continued)

(52) U.S. Cl.
CPC ... *A61B 17/1617* (2013.01); *A61B 17/320016* (2013.01); *A61B 17/320708* (2013.01); *A61B 17/320725* (2013.01); *A61B 2017/320791* (2013.01)

(58) Field of Classification Search
CPC .......... A61B 17/1608; A61B 17/1611; A61B 17/1657
USPC ...................................... 606/79, 84
See application file for complete search history.

(56) References Cited

U.S. PATENT DOCUMENTS

| 2,638,020 | A | | 4/1949 | Fischwick |
| 3,702,611 | A | * | 11/1972 | Fishbein ............... 606/81 |
| 3,866,601 | A | | 2/1975 | Russell |

(Continued)

FOREIGN PATENT DOCUMENTS

| DE | 3206782 A1 | 10/1982 |
| DE | 8806721 U1 | 7/1988 |

(Continued)

OTHER PUBLICATIONS

Surgical Technique Manual SK381-511, Wright Medical Technology, Inc., "Advanced Core Decompression System", PRO-DENSE® Core Decompression Procedure Kit, 12 pages, 2010.
(Continued)

*Primary Examiner* — Matthew Lawson
(74) *Attorney, Agent, or Firm* — Duane Morris LLP (57) ABSTRACT

A surgical device includes a housing, a cannula, a driving handle, and a cutting blade. The housing defines a hole in which the cannula that defines a passageway extending from a distal end to a proximal end is disposed. The driving handle is movably coupled to the housing and includes a driving rod slidably received within the passageway. The cutting blade is disposed within the passageway of the cannula and includes a distal end coupled to the distal end of the cannula, a proximal end configured to engage a distal end of the driving rod, and a reversibly deformable blade region disposed between the distal and proximal ends of the cutting blade. The deformable blade region is sized and configured to be received within at least one slot defined by the cannula and bends and straightens in response to movement of the driving handle relative to the housing.

12 Claims, 7 Drawing Sheets

(51) Int. Cl.
*A61B 17/32* (2006.01)
*A61B 17/3207* (2006.01)

(56) References Cited

U.S. PATENT DOCUMENTS

| | | | |
|---|---|---|---|
| 3,875,595 | A | 4/1975 | Froning |
| 4,203,444 | A | 5/1980 | Bonnell et al. |
| 4,467,800 | A | 8/1984 | Zytkovicz |
| 4,512,344 | A | 4/1985 | Barber |
| 4,545,374 | A | 10/1985 | Jacobson |
| 4,596,243 | A | 6/1986 | Bray |
| 4,601,290 | A | 7/1986 | Effron et al. |
| 4,700,702 | A | 10/1987 | Nilsson |
| 4,751,922 | A | 6/1988 | DiPietropolo |
| 4,984,564 | A | 1/1991 | Yuen |
| 5,015,255 | A | 5/1991 | Kuslich |
| 5,020,534 | A | 6/1991 | Pell et al. |
| 5,062,845 | A | 11/1991 | Kuslich et al. |
| 5,100,423 | A | 3/1992 | Fearnot |
| 5,108,404 | A | 4/1992 | Scholten et al. |
| 5,139,511 | A | 8/1992 | Gill et al. |
| 5,176,649 | A | 1/1993 | Wakabayashi |
| 5,269,785 | A | 12/1993 | Bonutti |
| 5,290,303 | A | 3/1994 | Pingleton et al. |
| 5,295,994 | A | 3/1994 | Bonutti |
| 5,310,406 | A | 5/1994 | Sharpe et al. |
| 5,313,962 | A | 5/1994 | Obenchain |
| 5,437,665 | A | 8/1995 | Munro |
| 5,439,464 | A | 8/1995 | Shapiro |
| 5,445,639 | A | 8/1995 | Kuslich et al. |
| 5,454,365 | A | 10/1995 | Bonutti |
| 5,472,426 | A | 12/1995 | Bonati et al. |
| 5,484,437 | A | 1/1996 | Michelson |
| 5,489,307 | A | 2/1996 | Kuslich et al. |
| 5,499,981 | A | 3/1996 | Kordis |
| 5,505,732 | A | 4/1996 | Michelson |
| 5,540,693 | A | 7/1996 | Fisher |
| 5,569,290 | A | 10/1996 | McAfee |
| 5,607,435 | A | 3/1997 | Sachdeva et al. |
| 5,669,926 | A | 9/1997 | Aust et al. |
| 5,697,889 | A * | 12/1997 | Slotman et al. ............... 600/204 |
| 5,700,291 | A | 12/1997 | Kuslich et al. |
| 5,762,629 | A | 6/1998 | Kambin |
| 5,797,941 | A | 8/1998 | Schulze et al. |
| 5,814,044 | A | 9/1998 | Hooven |
| 5,876,399 | A | 3/1999 | Chia et al. |
| 5,913,858 | A | 6/1999 | Calandruccio et al. |
| 5,928,239 | A | 7/1999 | Mirza |
| 5,957,884 | A | 9/1999 | Hooven |
| 6,001,116 | A | 12/1999 | Heisler et al. |
| 6,371,968 | B1 | 4/2002 | Kogasaka et al. |
| 6,383,188 | B2 | 5/2002 | Kuslich et al. |
| 6,383,195 | B1 | 5/2002 | Richard |
| 6,387,095 | B1 | 5/2002 | Kennett et al. |
| 6,440,138 | B1 | 8/2002 | Reiley et al. |
| 6,468,279 | B1 | 10/2002 | Reo |
| 6,863,672 | B2 | 3/2005 | Reiley et al. |
| 7,044,954 | B2 | 5/2006 | Reiley et al. |
| RE42,757 | E | 9/2011 | Kuslich et al. |
| 2007/0288042 | A1 | 12/2007 | Serbousek et al. |
| 2008/0114364 | A1* | 5/2008 | Goldin et al. .................. 606/79 |
| 2011/0184447 | A1 | 7/2011 | Leibowitz et al. |
| 2012/0101512 | A1 | 4/2012 | Locke et al. |

FOREIGN PATENT DOCUMENTS

| | | |
|---|---|---|
| DE | 4036804 A1 | 5/1992 |
| DE | 19639193 A1 | 4/1998 |
| WO | 92/08416 A1 | 5/1992 |

OTHER PUBLICATIONS

Surgical Technique Manual SK241-5101, Wright Medical Technology, Inc., "Advanced Core Decompression System", PRO-STIM™ Injectable Inductive Graft, 12 pages, 2010.

* cited by examiner

EXPANDABLE SURGICAL DEVICE

CROSS-REFERENCE TO RELATED APPLICATIONS

This application claims priority to U.S. Patent Application No. 61/441,406, which was filed on Feb. 10, 2011 and is herein incorporated by reference in its entirety.

FIELD OF DISCLOSURE

The disclosed device and method relate to surgical devices. More specifically, the disclosed device and method relate to expandable surgical devices for minimally invasive debridement.

BACKGROUND

In various types of surgical procedures, bones or tissue is debrided in an attempt to help heal the remaining tissue or bone. There exist many different types of surgical tools that are used to debride bone or tissue. However, many of these surgical tools require large (i.e., non-minimally invasive) openings to be created in order for the debriding tool to be used. The use of non-minimally invasive surgical techniques typically results in more operative trauma for the patient, longer recovery times, and increased scarring.

Accordingly, an improved debriding tool that may be used in a minimally-invasive incision is desirable.

SUMMARY

In some embodiments, a surgical device includes a housing, a cannula, a driving handle, and a cutting blade. The housing defines a hole in which the cannula that defines a passageway extending from a distal end to a proximal end is disposed. The driving handle is movably coupled to the housing and includes a driving rod slidably received within the passageway. The cutting blade is disposed within the passageway of the cannula and includes a distal end coupled to the distal end of the cannula, a proximal end configured to engage a distal end of the driving rod, and a reversibly deformable blade region disposed between the distal and proximal ends of the cutting blade. The deformable blade region is sized and configured to be received within at least one slot defined by the cannula and bends and straightens in response to movement of the driving handle relative to the housing.

A debridement method is disclosed in which a distal end of a cannula of a surgical device is inserted into a hole formed in a patient. A driving handle is axially moved in a first direction relative to a housing of the surgical device to deploy a reversibly deformable blade region of a cutting blade in situ. The axial movement of the driving handle relative to the housing bends the reversibly deformable blade region that is received through a slot defined by the cannula thereby deploying the reversibly deformable blade region in situ. The blade region debrides an area within the patient. The driving handle is axially moved in a second direction relative to the housing of the surgical device to retract the blade region into the cannula, and the distal end of the cannula of the surgical device is from the hole formed in the patient.

In some embodiments, a surgical instrument includes a housing including a pair of outwardly extending handles and an extension. The extension is disposed approximately perpendicular to the pair of handles and defining a hole therethrough. A cannula defines a passageway that extends from a proximal end disposed within the hole and coupled to the housing to a distal end that defines at least one slot. A driving handle is movably coupled to the housing and includes a driving rod slidably received within the passageway of the housing. A cutting blade is disposed within the passageway of the cannula. The cutting blade includes a distal end coupled to the distal end of the cannula, a proximal end configured to engage a distal end of a driving rod slidably disposed within the passageway, and a reversibly deformable blade region disposed between the distal and proximal ends of the cutting blade. The deformable blade region is sized and configured to be received within the at least one slot defined by the cannula and includes a first portion disposed at an angle with respect to a second portion. The angle between the first and second portions facilitates bending of the reversibly deformable blade portion, which bends and straightens in response to axial movement of the driving handle relative to the housing.

BRIEF DESCRIPTION OF THE DRAWINGS

These and other features and advantages of the present invention will be more fully disclosed in, or rendered obvious by the following detailed description of the preferred embodiments of the invention, which are to be considered together with the accompanying drawings wherein like numbers refer to like parts and further wherein.

DETAILED DESCRIPTION

This description of preferred embodiments is intended to be read in connection with the accompanying drawings, which are to be considered part of the entire written description. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral," and the like are to be interpreted relative to one another or relative to an axis of elongation, or an axis or center of rotation, as appropriate. Terms concerning attachments, coupling, and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

Figure 1:
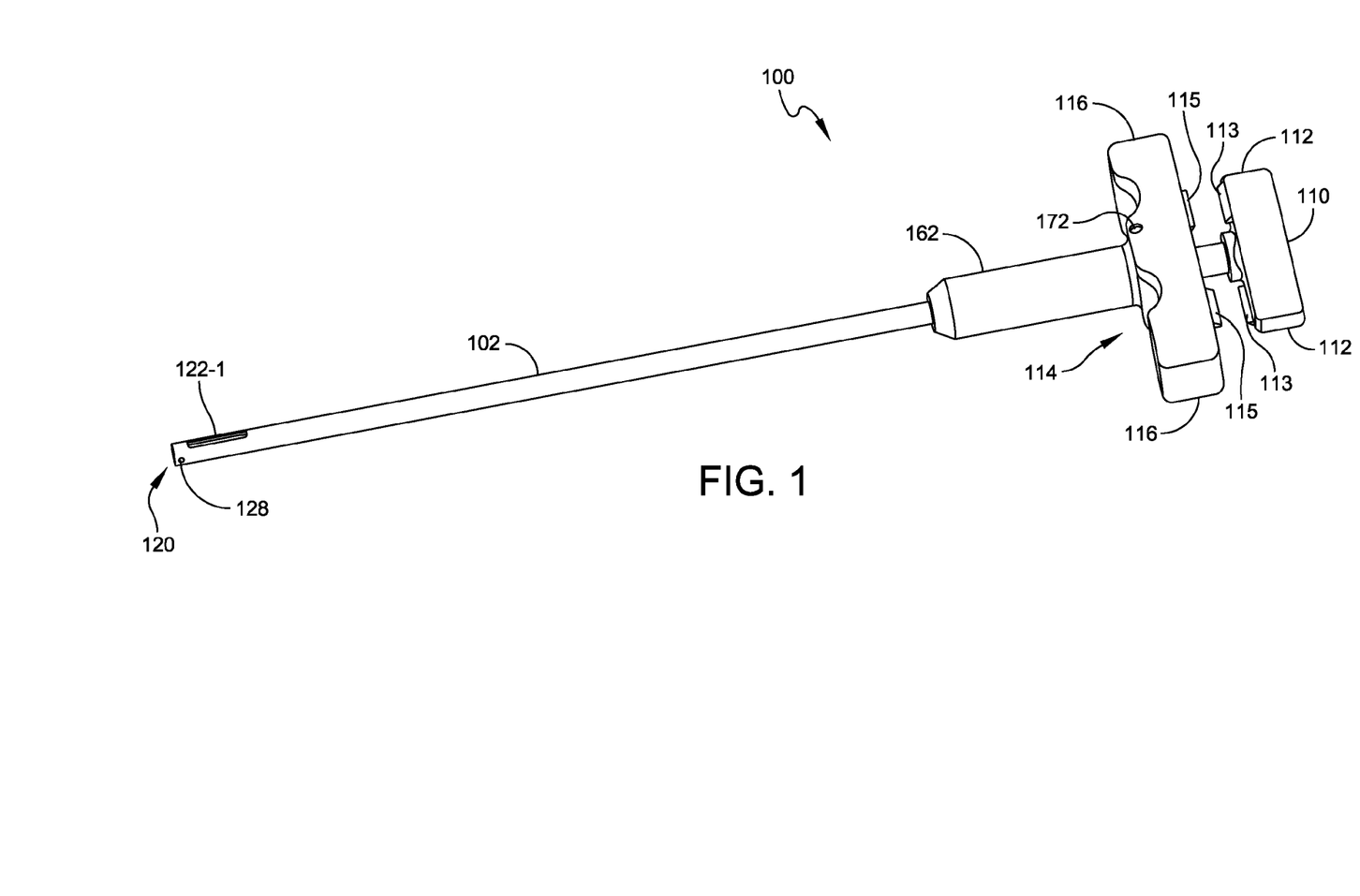
FIG. 1 is an isometric view of one example of an improved expandable device.
Figure 2:
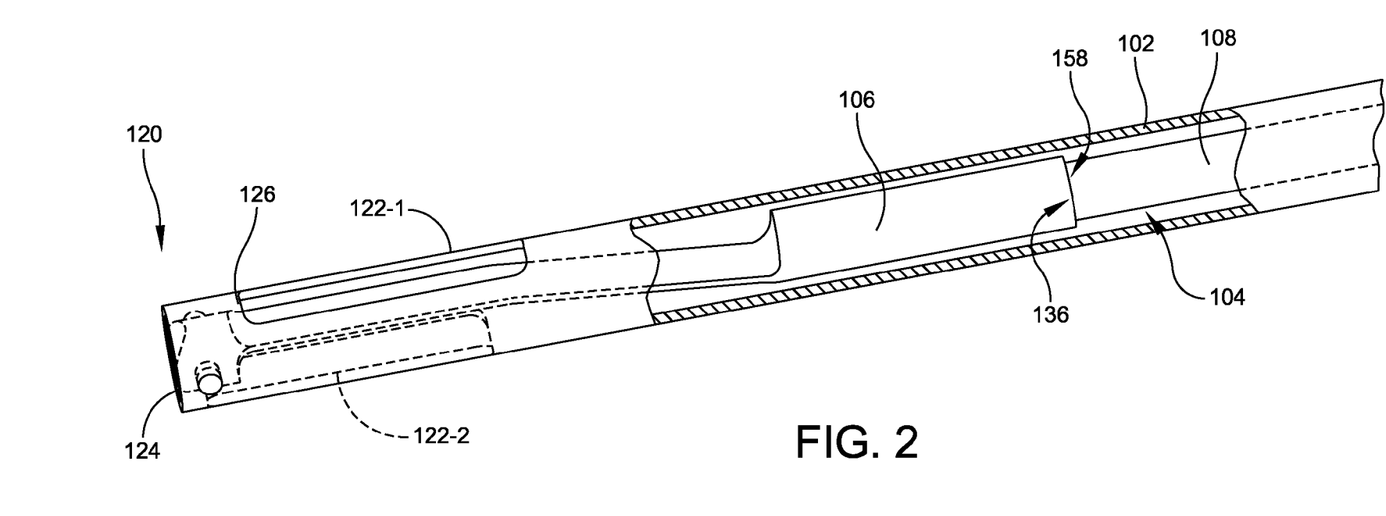
FIG. 2 is a sectional view of a cutting blade and driving rod disposed within a cannula of the expandable device illustrated in FIG. 1.
Figure 3:
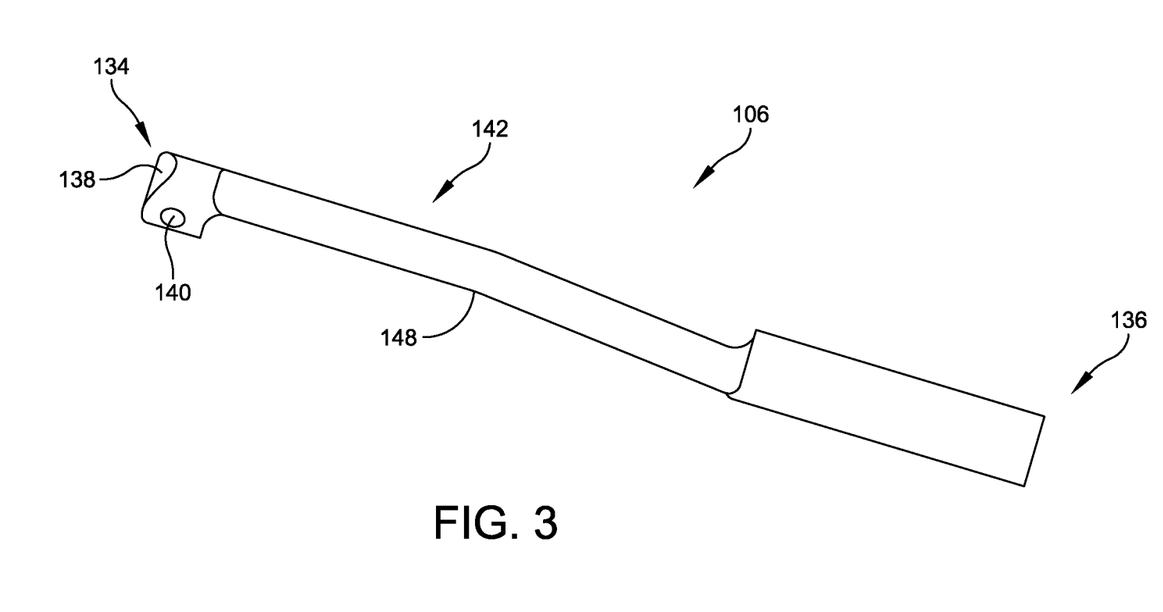
FIG. 3 is an isometric view of one example of a cutting blade in accordance with the expandable device illustrated in FIG. 1.
Figure 4:
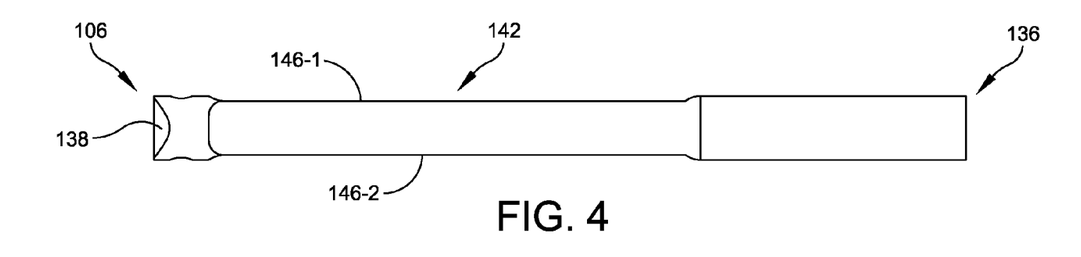
FIG. 4 is a top side view of the cutting blade illustrated in FIG. 3.
Figure 5:
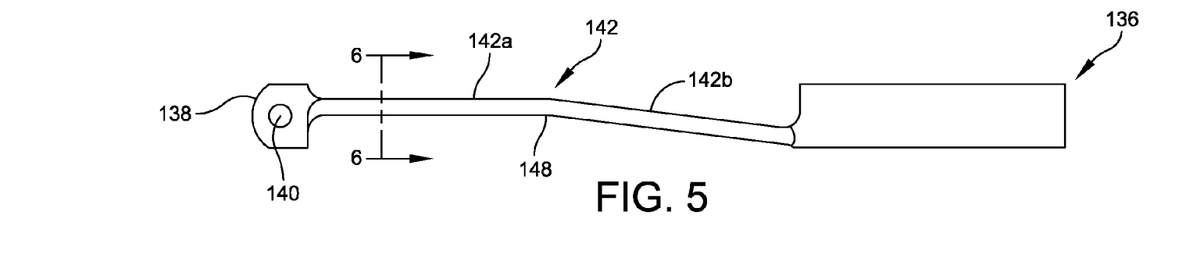
FIG. 5 is a side view of the cutting blade illustrated in FIG. 3.
Figure 6:
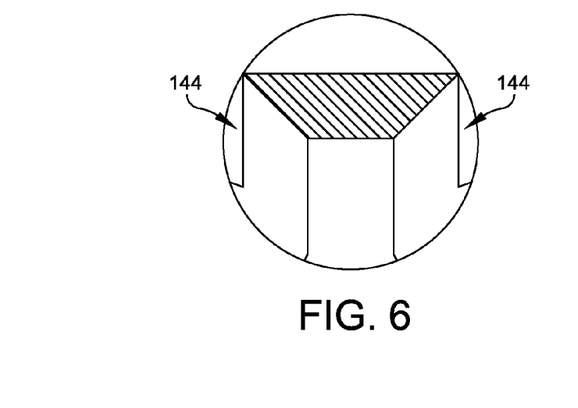
FIG. 6 is a sectional view of the cutting blade taken along line 6-6 in FIG. 5.
Figures 9, 10:
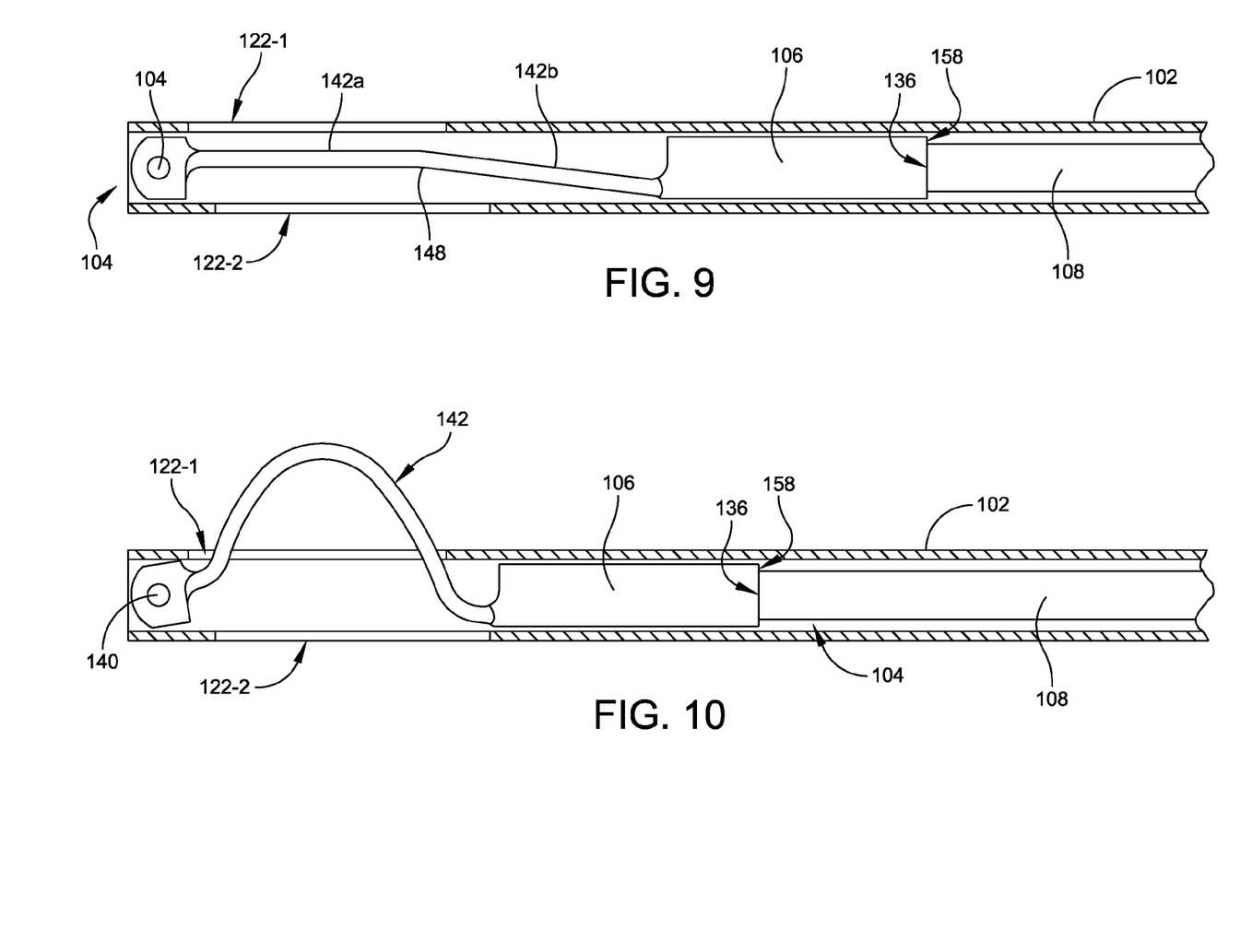
FIG. 9 illustrates the cutting blade retracted within the cannula.
FIG. 10 illustrates the cutting blade having been compressed and expanded from the slots defined by the cannula.

The example of an expandable device 100 illustrate in FIG. 1 includes a cannula 102 defining an internal passageway 104 sized and configured to slidably receive a cutting blade 106 and a driving rod 108 (FIGS. 2, 9, and 10). A driving handle 110 is coupled to or abuts a proximal end of driving rod 108 and includes one or more extensions 112 for providing a gripping surface. One or more shoulders 113 extend from the bottom surface of extensions 112. A housing 114 includes a pair of outwardly extending handles 116 and defines a central opening 118 sized and configured to receive driving rod 108 and driving handle 110. One or more shoulders 115 extend from the upper surfaces of handles 116 and are configured to cooperate with shoulders 113 to provide a rotational stop.

In one embodiment, cannula 102 is fabricated from stainless steel or other surgical grade material and has a length of approximately 16 cm (approximately 6.3 in). The internal passageway 104 may have a diameter of approximately 0.6 cm (approximately 0.236 in), although one skilled in the art will understand that passageway 104 may have other dimensions. Distal end 120 of cannula 102 defines a pair of rectangular slots 122-1, 122-2 (collectively referred to as "slots 122") disposed approximately 180 degrees from another adjacent to the distal tip 124 as best seen in FIG. 2. In some embodiments, slots 122 have a length of approximately 1.27 cm (approximately 0.5 in), a width of approximately 0.317 cm (approximately 0.125 in), and has a distalmost end 126 disposed approximately 0.3 cm (approximately 0.118 in) from distal tip 124, although one skilled in the art will understand the size of slots 122 may be smaller or larger. In some embodiments, one of the slots 122 may be hole of a smaller size than the size of slot 122.

A reamed hole 128 having a diameter of approximately 0.06 cm (approximately 0.024 in), for example, is disposed adjacent to distal tip 124. In some embodiments, the center of reamed hole 128 is disposed approximately 0.15 cm (approximately 0.059 in) from distal tip 124, although one skilled in the art will appreciate that reamed hole 128 may have different dimensions and be located at different positions along the length of cannula 102. Proximal end 130 of cannula 102 may also include a barb or protrusion 132 radially extending from cannula 102 for securing cannula 102 to housing 114 as described below.

Cutting blade 106 is fabricated from an elastic and/or reversibly deformable material such as spring steel, nitinol, or the like. As best seen in FIGS. 3-6, cutting blade 106 extends from a distal end 134 to proximal end 136 over a length of approximately 3.8 cm (approximately 1.5 inches). Distal end 134 includes a pair of chamfers or fillets 138 each having a radius of approximately 0.157 cm (approximately 0.062 in) and defines a hole 140 having a diameter of approximately 0.107 cm (approximately 0.042 in) that is centered approximately 0.13 cm (approximately 0.051 in) from distal end 134 of cutting blade 106.

A blade region 142 having a length of approximately 2.3 cm (approximately 0.91 in), a width of approximately 0.26 cm (approximately 0.10 in), and a thickness of approximately 0.076 cm (approximately 0.03 in) extends from a distance of approximately 0.26 cm (approximately 0.10 in) from distal end 134 of cutting blade 106. Cutting edges 144 (FIG. 6) are defined by a 45 degree taper formed along the lengthwise sides 146-1, 146-2 (collectively referred to as "lengthwise sides 146" or "sides 146") of blade region 142. Although two cutting edges 144 are illustrated, one skilled in the art will understand that blade region 142 may include fewer or more cutting edges 144. For example, blade region 142 may include a single cutting edge, or blade region 142 may include at least one edge having a plurality of serrations or cutting edges. A bend 148 is formed along the length of blade region 142 at the approximate midpoint of blade region 142 to facilitate blade region 142 bending to create a curette as described below. In some embodiments, bend 148 provides for an angle between zero and ten degrees between first portion 142a and second 142b of blade region 142; however, one skilled in the art will understand that bend 148 may provide for other angles between first and second portions 142a, 142b of blade region 142. Proximal end 136 may have a circular cross-sectional geometry with a diameter of approximately 0.3 cm (approximately 0.118 in) such that cutting blade 106 may be slidably received within cannula 102.

Figure 7:
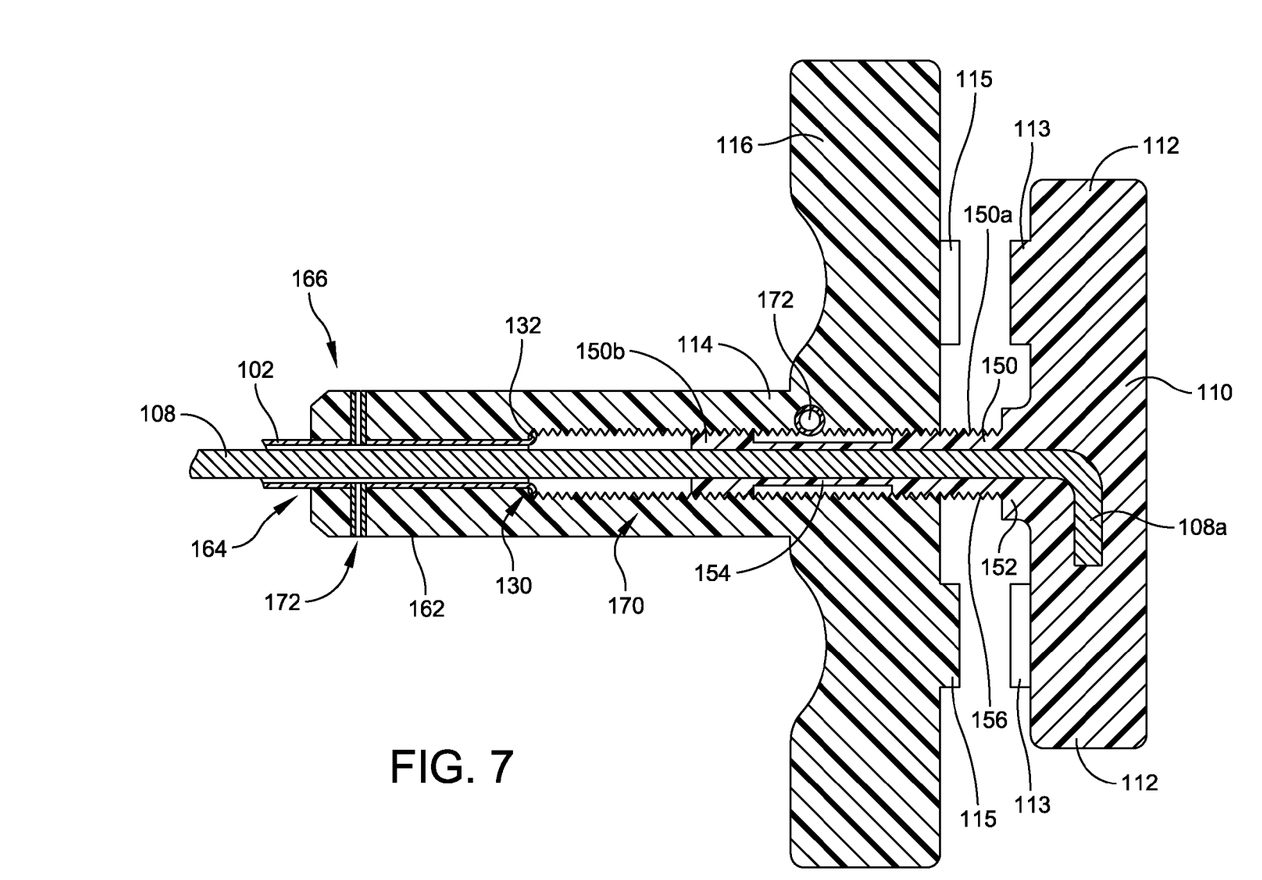
FIGS. 7 and 8 are a cross-sectional views of the proximal end of the expandable device illustrated in FIG. 1.
Figure 8:
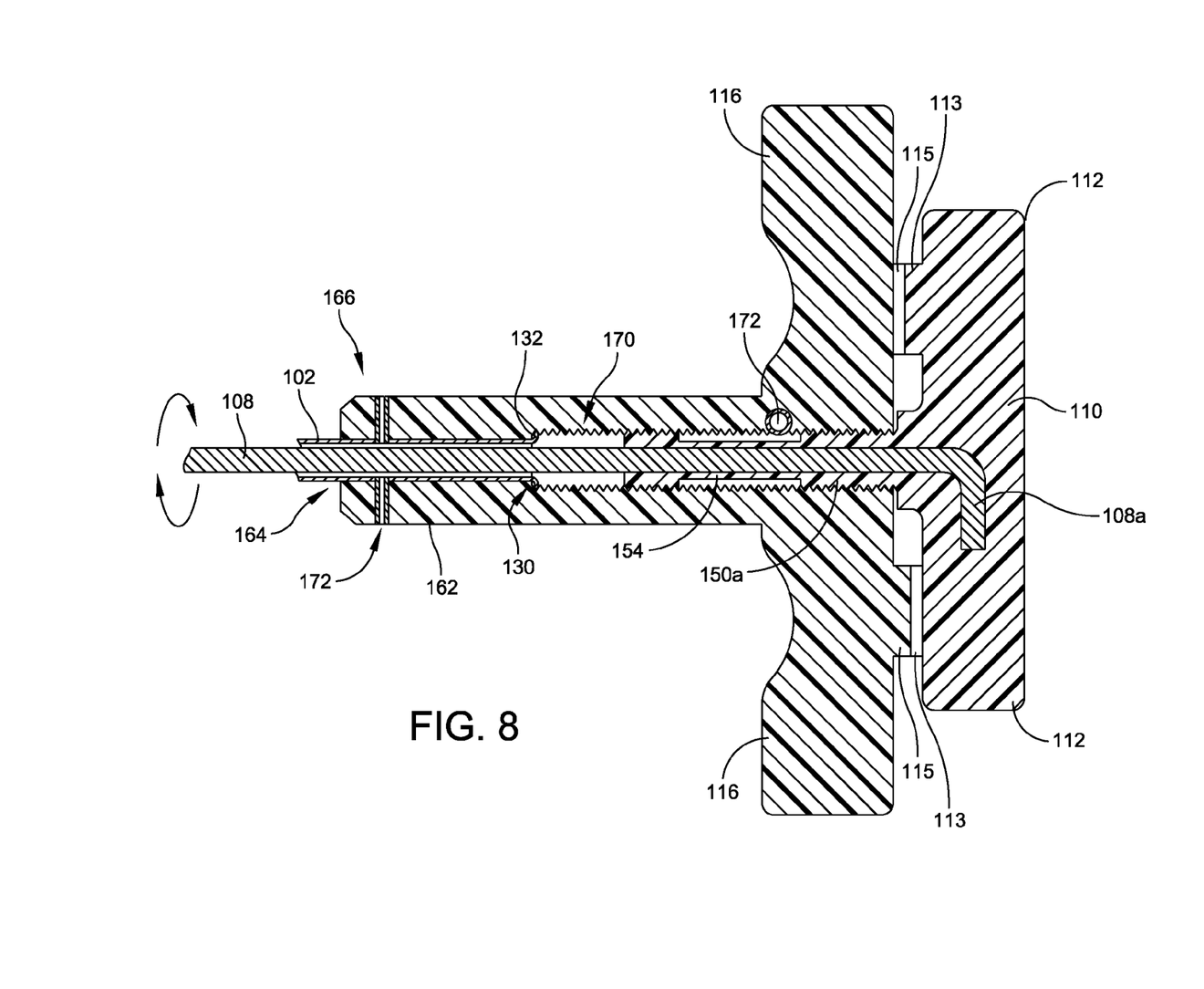

Turning now to FIGS. 7 and 8, driving rod 108 may be fabricated from a stainless steel or other sufficiently rigid material used in the surgical arts. In one embodiment, driving rod 108 has a length of approximately 18.89 cm (approximately 7.438 in) and a circular cross-sectional geometry with a diameter of approximately 0.25 cm (approximately 0.099 in) such that driving rod 108 may be slidably received within cannula 102. In some embodiments, driving rod 108 may include one or more rod members as will be understood by one skilled in the art. The proximal end of driving rod 108 includes an extension 108a that extends at an angle with respect to an axis defined by a longitudinal axis of driving rod 108. Extension 108a provides an area for driving handle 110 to be over-molded onto driving rod 108 and provides a failsafe mechanism for being able to advance and retract the blade 106 from cannula 102 in the event of damage to driving handle 110.

Still referring to FIGS. 7 and 8, driving handle 110 includes an elongate shaft 150 that extends from extensions 112 that form the base 152 of driving handle 110. Shaft 150 includes a reduced diameter or cross-sectional region 154 along its length that is disposed between adjacent regions 150a and 150b of shaft 150. In some embodiments, regions 150a and/or 150b of shaft 150 include threads 156 along their external surfaces. Distal end 158 of shaft 150 is configured to abut an end of driving rod 108 as illustrated in FIG. 2, although distal end 158 may define an aperture sized and configured to receive driving rod 108 therein and be cross-pinned together. In still other embodiments, driving rod 108 and shaft 150 of driving handle 110 are monolithic. Driving handle 110 may be fabricated from a polymer or plastic that is over-molded onto the proximal end of driving rod 108.

Housing 114 includes an extension 162 that defines a hole 164 that extends from the distal end 166 of housing 114 to proximal surface 168. Hole 164 has a diameter that is sufficient to slidably receive cannula 102, driving rod 108, and shaft 150 of driving handle 110 therein. In some embodiments, region 170 disposed between handles 116 along hole 164 is threaded such that the internal threads of region 170 are configured to engage threads 156 disposed along regions 150a and 150b of shaft 150. A reamed through or blind hole 172 disposed adjacent to, and partially intersecting, hole 164 is sized and configured to receive a dowel pin or spring pin as described below. Housing 114 may be machined from aluminum, steel, or molded from a plastic or polymer suitable for sterilization and use in the surgical field.

Expandable device 100 is assembled by inserting cannula 102 into hole 164 at the distal end 166 of housing 114. Set screws and/or dowel or spring pins (not shown) may be inserted into hole 172 using a press fit engagement as will be understood by one skilled in the art. The screws or pins inserted into holes 172 and contact the outer surface of cannula 102 to prevent rotation of cannula relative to housing 114. Barb/protrusion 132 of cannula 102 also works to prevent relative movement between cannula 102 and housing 114. Proximal end 130 of cutting blade 106 is inserted into cannula 102 until hole 140 at distal end 134 of cutting blade 106 aligns with reamed hole 128 disposed adjacent to distal end 120 of cannula 102. Once aligned, a pin (not shown) is inserted through holes 140 and 128 to cross pin cutting blade 106 to cannula 102. Cutting blade 106 is coupled to cannula 102 such that blade region 142 is aligned with slots 122 defined by cannula 102.

Driving rod 108 is inserted into hole 164 of housing 114 and into cannula 102. With driving rod 108 disposed within cannula 102, elongate shaft 150 of driving handle 110 is inserted into hole 164 of housing 114. In embodiments where regions 150a, 150b of shaft 150 include threads 156 as does region 170, driving rod 108 is rotated with respect to housing 114 until threads 156 of region 150b pass through threaded region 170 such that reduced diameter region 154 is disposed adjacent to threaded region 170. With reduced diameter region 154 disposed adjacent to threaded region 170, a dowel or spring pin (not shown) is inserted into hole 172 by a press fit engagement to prevent driving handle 110 from being removed from its engagement with housing 114. In embodiments where region 150b is not threaded and region 150a is threaded, then region 150a is inserted passed threaded region and a dowel or spring pin is inserted into hole 172.

In use, distal end 120 of cannula 102 is inserted into a minimally invasive hole made in a patient's body with cutting blade 106 disposed within cannula 102. Once cannula 102 has been inserted to the desired depth within the patient, a surgeon rotates driving handle 110 relative to housing 114 (i.e., in a clockwise or counterclockwise direction) such that threads 156 disposed on region 150a engage threaded portion 170 thereby moving elongate shaft 150 distally into hole 164. As elongate shaft 150 is urged towards distal end 120 of cannula 102, distal end 160 of shaft 150 contacts driving rod 108 and forces distal end 158 of driving rod 108 into abutment with proximal end 136 of cutting blade 106 as illustrated in FIG. 9.

Further rotation of driving handle 110 relative to housing 114 causes blade region 142 to bend and emerge from one of the slots 122 (e.g., slot 122-1) defined by cannula 102 in situ as illustrated in FIG. 10. The rotation of driving handle 110 relative to housing 114 may continue until threaded region 150a of driving handle 110 is fully received within housing 114, blade region 142 contacts bone, the physician determines that a sufficient amount of blade region 142 has been deployed, shoulder(s) 113 of driving handle 112 contact shoulder(s) of handles 116, or the occurrence of another event as will be understood by one skilled in the art.

The example of an expandable device 100 illustrate in FIG. 1 includes a cannula 102 defining an internal passageway 104 sized and configured to slidably receive a cutting blade 106 and a driving rod 108 (FIGS. 2, 9, and 10). A driving handle 110 is coupled to or abuts a proximal end of driving rod 108 and includes one or more extensions 112 for providing a gripping surface. One or more shoulders 113 extend from the bottom surface of extensions 112. A housing 114 includes a pair of outwardly extending handles 116 and defines a central opening 118 sized and configured to receive driving rod 108 and driving handle 110. One or more shoulders 115 extend from the upper surfaces of handles 116 and are configured to cooperate with shoulders 113 to provide a rotational stop.

Once blade region 142 has been fully deployed or deployed a desired amount, the surgeon grasps housing 114 and debrides the bone with blade region 142. Such debridement may be performed by grasping handles 116 of housing 114 and rotating housing 114, and consequently expandable device 100, about an axis defined by cannula 102. Alternatively or additionally, the surgeon or other operator of device 100 may pivot device 100 about the approximate site where cannula 102 enters the body of the patient. One skilled in the art will understand that other motions may be used to debride a bone using device 100.

To remove device 100 from the patient, the surgeon rotates driving handle 110 with respect to housing 114 in the opposite direction (i.e., in a counterclockwise or clockwise direction) that the surgeon rotated driving handle 110 with respect to housing 114 to deploy blade region 142. Such rotation of driving handle 110 relative to housing 114 results in elongate shaft 150 being urged towards proximal end 130 of cannula 102 due to the engagement between threaded portion 170 of housing 114 and threads 156 disposed on region 150a of elongate shaft 150.

As driving handle 110 axially moves in a proximal direction, the compressive force exerted on cutting blade 106 by driving rod 108 and driving handle 110 is reduced and the spring force of cutting blade 106 causes the blade region 142 to return to equilibrium, i.e., its substantially straight form. Any bone or tissue matter trapped in the underside of the blade may exit cannula 102 through the second slot 122-2. Driving handle 110 is rotated and axially moved in a proximal direction relative to housing 114 until cutting blade is disposed within cannula 102 at which point the surgeon may retract device 100 from the patient's body.

The surgical device and method disclosed herein advantageously enables the blade to be deployed in situ, which enables the surgical device to be inserted through a minimally invasive incision. Additionally, the blade of the surgical device disclosed herein may be deployed to various distances thereby providing a surgeon with increased flexibility in the amount bone or tissue that is to be debrided.

Although the surgical device and method have been described in terms of exemplary embodiments, they are not limited thereto. Rather, the appended claims should be construed broadly, to include other variants and embodiments of the surgical device and method, which may be made by those skilled in the art without departing from the scope and range of equivalents of the device and method.

What is claimed is:

1. A surgical device, comprising:
  a housing defining a first hole therethrough in a first direction and a second hole in a second direction, the second hole receiving a pin therein;
  a cannula having a proximal end disposed within the first hole and coupled to the housing, the cannula defining a passageway extending from the proximal end to a distal end that defines at least one slot;
  a driving handle movably coupled to the housing, the driving handle including a base portion having a pair of opposed extensions each providing a respective gripping surface, a shaft extending from the base portion and being sized and configured to be received within a portion of the first hole defined by the housing, the shaft including a first portion having a reduced diameter with respect to a second portion of the shaft and a third portion of the shaft between which the first portion is disposed, and a driving rod coupled to at least one of the shaft and the base portion of the driving handle and being slidably received within the passageway defined by the cannula; and a cutting blade disposed within the passageway of the cannula and including a distal end coupled to the distal end of the cannula, a proximal end configured to engage a distal end of the driving rod, and a reversibly deformable blade region disposed between the distal and proximal ends of the cutting blade, the deformable blade region sized and configured to be received within the at least one slot defined by the cannula, wherein the deformable blade region bends in response to rotational movement of the driving handle and driving rod relative to the housing in a third direction that causes the driving handle and driving rod to move axially toward the distal end of the cannula, and the deformable blade region straightens in response to rotational movement of the driving handle and driving rod relative to the housing in a fourth direction that causes the driving handle and driving rod to move axially away from the distal end of the cannula, and wherein the first, second, and third portions of the shaft of the driving handle are configured to engage the pin received within the second hole defined by the housing to prevent the driving handle from being disengaged from the housing while permitting axial and rotational movement of the driving handle and the driving rod relative to the housing.

2. The surgical device of claim 1, wherein the hole defined by the housing is at least partially threaded.

3. The surgical device of claim 2, wherein at least one of the second and third portions of the shaft of the driving handle includes threads that are configured to engage the partially threaded hole defined by the housing, and wherein rotational movement of the driving handle relative to the housing provides the axial movement of the driving handle relative to the housing.

4. The surgical device of claim 1, wherein the reversibly deformable blade region includes a pair of opposed edges for debriding bone.

5. The surgical device of claim 1, wherein the reversibly deformable blade region includes a first portion disposed at an angle with respect to a second portion, the angle between the first and second portions for facilitating the bending of the blade portion.

6. The surgical device of claim 1, wherein the housing includes at least one shoulder extending proximally and the driving handle includes at least one shoulder extending distally, and wherein the at least one shoulder of the housing and the at least one shoulder of the handle are configured to engage one another to provide a rotational stop to prevent the driving handle from being further rotated in the third direction and moved distally relative to the housing.

7. The surgical device of claim 1, wherein the first direction is different from the second direction.

8. A surgical instrument, comprising:
a housing defining a hole therethrough;
a cannula coupled to the housing and defining a passageway extending from a proximal end of the cannula that is disposed within the hole defined by the housing to a distal end of the cannula that defines at least one slot;
a driving handle movably coupled to the housing and including
a driving rod slidably received within the passageway defined by the cannula and within the hole defined by the housing,
a base portion having a pair of opposed extensions, and
a shaft extending from the base portion and being sized and configured to be received within a portion of the hole defined by the housing, the shaft including a first portion having a reduced diameter with respect to a second portion of the shaft and a third portion of the shaft between which the first portion is disposed; and
a cutting blade disposed within the passageway of the cannula and including
a distal end coupled to the distal end of the cannula,
a proximal end configured to engage a distal end of a driving rod slidably disposed within the passageway, and
a reversibly deformable blade region disposed between the distal and proximal ends of the cutting blade, the deformable blade region sized and configured to be received within the at least one slot defined by the cannula and including a first portion disposed at an angle with respect to a second portion, the angle between the first and second portions for facilitating bending of the reversibly deformable blade portion,
wherein the deformable blade region bends and straightens in response to axial movement of the driving rod relative to the housing, and
wherein the first portion, second portion, and third portion of the shaft are configured to maintain the driving handle coupled to the housing while permitting axial and rotational movement of the driving rod relative to the housing.

9. The surgical device of claim 8, wherein the hole defined by the housing is at least partially threaded.

10. The surgical device of claim 9, wherein at least one of the second and third portions of the shaft is threaded and configured to engage the partially threaded hole defined by the housing, and wherein rotational movement of the driving handle relative to the housing provides the axial movement of the driving rod relative to the housing.

11. The surgical device of claim 8, wherein the reversibly deformable blade region includes a pair of opposed edges for debriding bone.

12. The surgical device of claim 8, wherein the housing includes at least one shoulder extending proximally and the driving handle includes at least one shoulder extending distally, and wherein the at least one shoulder of the housing and the at least one shoulder of the handle are configured to engage one another to provide a rotational stop that prevents the driving handle from being rotated beyond a certain point in a single direction.

\* \* \* \* \*